US006455849B1

(12) United States Patent
Hilton et al.

(10) Patent No.: US 6,455,849 B1
(45) Date of Patent: Sep. 24, 2002

(54) NORMAL METAL BOUNDARY CONDITIONS FOR MULTI-LAYER TES DETECTORS

(75) Inventors: Gene C. Hilton; John M. Martinis, both of Boulder; Kent D. Irwin, Lyons; David A. Wollman, Louisville, all of CO (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 14 days.

(21) Appl. No.: 09/671,620

(22) Filed: Sep. 28, 2000

Related U.S. Application Data

(60) Provisional application No. 60/157,741, filed on Oct. 5, 1999.

(51) Int. Cl.[7] ............................................. H01L 39/00
(52) U.S. Cl. .................................................. 250/336.2
(58) Field of Search ..................... 250/336.2; 374/183, 374/185; 338/18, 25; 505/847, 848, 849

(56) References Cited

U.S. PATENT DOCUMENTS

| | | | |
|---|---|---|---|
| 3,506,913 A | 4/1970 | Lambe et al. | 324/248 |
| 4,403,189 A | 9/1983 | Simmonds | 324/248 |
| 4,491,795 A | 1/1985 | Gelinas | 324/248 |
| 5,053,706 A | 10/1991 | Ohkawa | 324/248 |
| 5,162,731 A | 11/1992 | Fujimaki | 324/248 |
| 5,185,527 A | 2/1993 | Bluzer | 250/336.2 |
| 5,302,580 A | 4/1994 | Shimizu et al. | 505/233 |
| 5,306,521 A | 4/1994 | Shimizu et al. | 427/62 |
| 5,309,095 A | 5/1994 | Ahonen et al. | 324/248 |
| 5,480,861 A | 1/1996 | Tanaka et al. | 505/236 |
| 5,532,485 A | 7/1996 | Bluzer et al. | 250/336.2 |
| 5,596,206 A | 1/1997 | Yamazaki | 257/30 |
| 5,634,718 A | 6/1997 | Martinis et al. | 374/32 |
| 5,641,961 A | 6/1997 | Irwin et al. | 250/336.2 |
| 5,710,437 A | 1/1998 | Kurakado et al. | 257/32 |
| 5,753,935 A | 5/1998 | Kurakado et al. | 257/31 |
| 5,760,463 A | 6/1998 | Hato | 257/662 |
| 5,866,252 A | 2/1999 | de Rochemont et al. | 428/373 |
| 5,880,467 A | 3/1999 | Martinis et al. | 250/310 |
| 5,880,468 A | 3/1999 | Irwin et al. | 250/336.2 |
| 6,239,431 B1 * | 5/2001 | Hilton et al. | 250/336.2 |

OTHER PUBLICATIONS

D.A. Wollman et al., "High–Resolution, Energy–Dispersivemicrocalorimeterspectrometer Forx–Raymicroanalysis", *National Institute of Standards & Technology*, pp. 1–25.

G.C. Hilton et al., "Superconducting Transition–Edge Microcalorimeters For X–ray Microanalysis", *National Institute of Standards & Technology*, Sep. 15, 1998, pp. 1–5.

* cited by examiner

*Primary Examiner*—Constantine Hannaher
*Assistant Examiner*—Shun Lee
(74) *Attorney, Agent, or Firm*—Millen, White, Zelanoo & Branigan, P.C.

(57) ABSTRACT

Multi-layer transition-edge sensors (TES) having improved performance, a method for preparing them and methods of using them. Specifically, the improvement lies in providing normal metal strips along the edges of the superconducting and normal metal layers parallel to the current flow in the TES during operation. These strips (referred to as "banks") provide for both improved detector performance and improved detector robustness against corrosion. This improvement is an important advance particularly for TES-based microcalorimeter detectors. The improved TESs also have many other applications based on the very precise thermometer function achieved by the TES.

37 Claims, 4 Drawing Sheets

NORMAL METAL BOUNDARY CONDITIONS FOR MULTI-LAYER TES DETECTORS

This application claims benefit under 35 U.S.C. §119 of the provisional application, U.S. Ser. No. 60/157,741, filed Oct. 5, 1999.

Described herein are multilayer transition-edge sensors (TES) having improved performance, a method for preparing them and methods of using them. Specifically, the improvement lies in providing normal metal strips along the edges of the superconducting and normal metal layers parallel to the current flow in the TES during operation. These strips (hereinafter referred to as "banks") provide for both improved sensor performance and improved sensor robustness against corrosion. This improvement is an important advance particularly for the TES-based microcalorimeter detectors. The improved TES also have many other applications based on the very precise thermometer function achieved by the TES, as further discussed below. Such further applications are also contemplated by this invention.

BACKGROUND OF THE INVENTION

A wide variety of particle and energy detectors and other devices can be made using a superconducting TES as a thermometer; see, e.g., Wollman et al., *High-resolution, Energy-dispersive Microcalorimeter Spectrometer for X-ray Microanalysis, J. Microscopy* 188(3), pp. 196–223 (Dec. 3, 1997); and, Hilton et al., *Superconducting Transition-edge Microcalorimeters for X-ray Microanalysis, IEEE Transactions on Applied Superconductivity*, 9(2), pp. 3177–3181 (June 1999); both of which are incorporated by reference herein in their entirety. By operating the device such that the TES is held within its superconducting transition temperature region (i.e., the temperature region in which the material switches from normal conducting to superconducting property) any heat deposited in the TES can be very precisely measured due to the strong dependence of its conductivity (or conversely electrical resistance) on the temperature. Thus, very precise measurement and/or detection of a particle or energy source which provides even a minute heating effect can be performed. It is known that bilayers (and other multilayers) of superconductors with normal metals can provide excellent TES-based detectors; see, particularly Irwin et al. (U.S. Pat. No. 5,880,468) which is incorporated herein by reference in its entirety. For example, such multi-layers provide the ability to independently control the superconducting transition temperature ($T_c$) and the heat diffusion properties of the TES. However, without careful consideration of materials compatibility and fabrication techniques, multilayer TESs may have difficulties not observed in homogeneous TESs. These difficulties arise primarily in two areas, environmental or electrochemical degradation of the bilayer, and non-uniform conductivity at the edges of the TES.

The invention described here pertains to efforts made which overcame these difficulties.

SUMMARY OF THE INVENTION

For a TES to have low-noise operation it is important that the edges of the layer(s) parallel to the direction of current flow have uniform electrical conductivity. (The physical "edges" of the TES layers discussed here, also referred to as "outer sides" herein, should not be confused with the "transition edge" which pertains to the temperature "edge" between superconducting and normal properties). If some portion of the physical edges are superconducting and other portions are in the normal state, there will be non-uniform critical current along the length of the TES, causing phase-slip behavior and excess noise. Thus, the TES should be made as close as possible to either fully superconducting or fully normal boundary conditions.

While the increased critical currents obtained in detectors with fully superconducting boundary conditions offer somewhat improved performance over detectors with fully normal boundary conditions, bilayers (and thus multilayers) with superconducting boundary conditions are very difficult to achieve. Using Usadel theory, we calculated that if the superconducting layer of the TES is as little as 20 nm wider than the normal-metal layer, there will be a small region with a $T_c$ higher than the bulk of the TES. It is also important that the interface between normal and superconducting layers be protected. Any corrosion of the interface along the film edges may decrease the proximity coupling of the layers leading to effects similar to those discussed above. Many of the material combinations suitable for use as multilayers suffer from strong electrochemical effects, which are likely to cause extensive edge corrosion. Problems such as these are often solved using an edge passivating film such as $SiO_2$ or $Si_3N_4$. However, for TES based x-ray and infrared detectors, this approach may be undesired because of energy loss due to energy trapping in the passivating film.

The most obvious method for fabricating a structure with normal-metal boundary conditions is to deposit a bilayer with normal metal on the bottom and patterning the two layers such that the upper superconducting layer is narrower than the base normal layer. We have fabricated such a structure using our preferred bilayer materials (Cu/Mo). A plot of the resistive transition versus temperature is shown by curve A of FIG. 1. The transition is very broad with a "knee" indicative of two transition temperatures. It is believed that this poor transition can be attributed primarily to stress effects in the Mo superconducting layer, since refractory films such as Mo tend to be difficult to grow on softer films such as Cu. It is likely there is either stress cracking or delamination along the edge of the bilayer, leading to a variation in proximity-effect coupling across the width of the bilayer.

It is also possible to create a bilayer with normal-metal boundary conditions by depositing a bilayer with the superconductor on the bottom. The two layers are then etched, with the superconducting layer being over-etched so the top normal metal layer overhangs to obtain normal-metal boundary conditions. The resistive transition of such a structure is plotted in curve B of FIG. 1. This transition, while greatly improved compared to curve A, also shows some undesirable structure. It is believed that this structure can be attributed to environmental effects such as corrosion at the bilayer edges.

According to the invention, therefore, a greatly improved superconducting transition can be achieved by adding normal metal "banks" covering the outer sides, i.e, "edges", of the multilayer TES parallel to the direction of current flow. If the structure of the layers is not square or rectangular the banks would cover the outer sides other than those through which the current flows, i.e., other than those which contain the leads. The banks are provided to cover the edges such that normal-metal boundary conditions are achieved. Such a structure is exemplified by FIG. 2. There, an additional normal metal deposition and patterning is conducted to form the banks and provide both fully normal state boundary conditions and passivation of the bilayer sidewalls. By providing such banks, the preferably fully normal-metal boundary conditions are achieved and the disadvantages discussed above in providing superconducting boundary conditions or providing normal-metal boundary conditions in other insufficient ways are avoided.

The normal metal used to form the banks may be any of the normal metals described below for use as the normal metal layer(s) in the multilayer TES. It is particulary preferred that the same normal metal for both the banks and the TES layer be used, thus leaving no exposed edges of dissimilar normal metals which may lead to corrosion at such exposed interfaces. In one embodiment, the banks and the normal metal layer as the top layer of the multilayer TES are deposited in a single step as an integral structure.

The banks can be provided on the TES by any of the known metal film deposition and photoresist patterning techniques and the layers of the TES can be provided by the same known techniques. Preferably such a process is conducted by vacuum deposition wherein the metal is evaporated by thermal evaporation or electron evaporation or by sputtering, for example. Of particular preference for fabricating the banks and the TES layers is e-beam evaporation using shadow masks to define the deposition area, including providing the leads and any other desired structure. It is preferred that the fabrication be conducted so as to minimize the need to break the vacuum which could lead to formation of a contamination layer. Although, it is also possible to break vacuum and then etch the contaminant layer in situ. Preferably, whenever it is necessary to break the vacuum to perform a different step, the surfaces will be cleaned by known methods before further depositing is conducted. The layer thickness can be monitored during deposition with a quartz crystal which is preferably placed near the substrate. Details of e-beam evaporation and of alternative deposition techniques, such as sputtering, are known to those skilled in the art. The patterning of the layers can be conducted by wet etching or plasma etching, for example, in a manner known in the art.

The banks are provided to cover the edges parallel to the current flow in the typical square or rectangular-shaped TES. In an irregularly shaped TES, which is within the contemplation of this invention, the banks would preferably be provided on any edges which do not contain the leads. The banks are provided to a thickness and depth sufficient such that the edges with the banks exhibit an essentially fully normal-metal boundary condition. This, generally, can be assured if the banks result in a transition temperature of the edges of 5% or more lower than the transition temperature of the TES layers. In a further non-limiting embodiment the banks can be provided to about twice the thickness of the layer(s) they are covering.

The normal-metal layer(s) and the banks are made of any metal or metal alloy which is a normal conductor at the operating temperature of the TES sensor. It is preferred that the normal metal not rapidly form a contaminant layer, such as an oxide, so as to minimize impurity at the superconductor layer interface. Preferred normal metals include gold, silver, copper, palladium, platinum, gold/copper alloys and palladium/gold alloys. For applications requiring high resistance detectors, high sheet resistance resistance materials such as alloys would be advantageous. The normal metal can also be a ferromagnetic material such as chromium, manganese, iron, cobalt and nickel, in which case the $T_c$ of the bilayer is suppressed well below the $T_c$ of the superconductor with only a thin normal-metal layer. The normal metal can also be a material such as tungsten which is a superconductor having a $T_c$ below the operating temperature of the sensor, but is a normal conductor at the operating temperature.

The superconducting layer(s) may be of any metal which provides superconducting properties, particularly where such properties are exhibited at a temperature of 0.3 to 4 K. Preferred examples thereof are Mo, Ti, Al, Zr, W, Ir, Ta and Hf, with Mo being particularly preferred. The transition temperature of the TES having layers of normal metal and the superconductor is lower than that of the superconducting metal alone and the combination of the normal metal layer or layers and the superconducting layer or layers should be selected to provide a transition temperature and transition temperature width fulfilling the needs of the ultimate application of the TES. The thickness of the respective layers and the other structural aspects of the TES will also affect the properties thereof. Bilayers of Mo—Cu, Mo—Au and Ti—Au may be particularly useful when used in connection with the banks of the invention.

The thickness of the normal metal and superconducting layers in the TES will fall within the range of the minimum thickness in which they can be deposited into a continuous layer, e.g., about 5.0 nm, and the maximum thickness which still allows an interaction between the layers to provide a TES effect, e.g., about 10 $\mu$m. More preferably the layers are within the range of 0.01 $\mu$m to 0.5 $\mu$m.

A preferred structure of the TES according to the invention is shown in FIG. 2 wherein the TES is a bilayer having a base superconductor on the substrate with the leads integral with and on opposing sides of this layer, a normal metal layer thereon which is inside the edges of the superconductor layer and normal metal banks covering the edges of both layers on the sides without the leads. However, the inventive aspect of the banks providing a normal-metal boundary condition can be applied to any other TES of two or more layers. For example, a bilayer with the normal metal layer as the base layer and the superconducting layer above it, a trilayer with a normal metal layer sandwiched between two superconducting layers of the same or different superconductors, a trilayer with a superconductor layer sandwiched between two normal metal layers of the same or different metals or a TES with even further layers of normal and superconducting metals. In any embodiment wherein the top layer is a normal metal layer, such top layer and the banks may be formed in a single step as an integral structure; see, e.g., FIG. 4.

The substrate is a material which has lower conductivity than the multilayer TES so that it does not create a conducting path around the TES. It is also preferably a material which is not a source of impurities to the layers of the TES. In a preferred embodiment, the substrate is crystalline silicon coated with a $SiN_x$ layer. In another preferred embodiment the substrate is a $SiN_x$ membrane having low thermal conductivity. Substrates of Si, $Si_3N_4$ and $SiO_2$ are also preferred. The substrate can also serve as a substrate for a particle absorber and for measurement circuit connections.

In operation, the TES is maintained in the transition region where its properties are extremely sensitive to temperature. The TES will have a superconducting state, a normal conducting state and a transition region between them. The conductivity state of the TES depends on the operating temperature, and the conductivity changes rapidly with temperature within the transition region. The transition region is characterized by a transition temperature, $T_c$, and by a transition width. The term transition region may be used in lieu of transition edge to emphasize the fact that the transition is not instantaneous but rather requires a finite temperature range. In operation, the TES is cooled to a temperature within or below the transition region, wherein small changes in temperature produce large changes in the TES conductivity properties. This gives the TES the ability of high precision detection and/or measurement of temperature and thus it can be adapted for use in any device for high precision detection and/or measurement of any particle single photon or other energy source which will evoke a temperature change either by itself or through some other component, such as an x-ray absorber.

When used as a particle detector, such as for x-ray detection, the energy of an absorbed particle is converted to heat by an absorber and the transition from the TES's superconducting state to normal state is used to sense the temperature rise. The transition temperature, $T_c$, of the TES can be reproducibly controlled as a function of the materials, the relative thicknesses and the total thickness of the superconducting and normal-metal layers. The range of available $T_c$'s preferably extends from about 5 mK to above 1 K, for example, preferably from 50 mK to 500 mK, allowing the detector to be tailored to the particular application. For x-ray detection the preferred $T_c$ is about 50–150 mK. The width of the transition edge, i.e., the temperature range in which the superconducting layer shifts from fully normal to fully superconductive state, varies depending upon a number of factors. For example, the detector can provide a width of the transition edge from anywhere less than the $T_c$ less than 0.1 mK. Typical, non-limiting examples provide widths from 0.05 to 0.5 mK. In one non-limiting embodiment, detectors with a width of transition edge less than 0.1 mK, e.g., down to the lowest measurable width, can be provided to allow very high detector sensitivity.

The detector can be used with many types of particles, including photons, molecules, electrons, ions and phonons. In a preferred embodiment the particles are x-ray photons. Depending on the type of particle, the x-ray absorber can be a normal metal, a superconductor, semiconductor, an insulator, the TES substrate, or the TES itself. In a preferred embodiment the absorber is a normal metal or a semi-metal, such as Bi.

In a further embodiment, the particles are infrared photons and the TES is used as a detector in an infrared bolometer, which can be used, for example, for infrared astronomy applications. In a bolometer the total incident power is measured as opposed to a microcalorimeter which responds to individual particles.

The TES can also be used to detect ions, especially large ions. In time-of-flight mass spectroscopy of large ions such as biopolymers there is a need for particle detectors which are efficient even for high masses. For large ion detection, a long narrow TES multilayer fabricated in a meandering pattern to maximize sensitive area is especially suitable because it provides high speed.

The transition edge sensor of this invention can further be used as a thermometer to measure the temperature of an object. For such application, the TES is thermally coupled with the object. The particle detector is a special case wherein the object is a particle absorber. The thermometer is well adapted to accurate temperature measurement because it is particularly sensitive to changes in temperature. Electrothermal feedback within the thermometer can be used to regulate the TES temperature and thereby regulate the temperature of an object thermally coupled therewith. For a thermometer, it may be desired to have a broader transition width so that there is a greater operating range. To provide the desired R vs T profile, the superconducting and/or normal-metal layer can have a graded thickness. The R vs T profile can also be designed with, for example, a broad transition region which has within it a portion having a sharper transition edge. This profile gives regulation over a broad range with precise temperature control within a target range. Similarly other profiles can be designed for specific applications.

To maintain the TES within the transition region, electrothermal feedback (ETF) may be utilized for temperature regulation, for example. An example of use of ETF is provided in U.S. Pat. No. 5,641,961. Among other possibilities for maintaining the temperature in the transition region is careful control of the cryogenic cooling. The transition from superconducting to normal conducting is measured to determine the energy deposited in the system by particles. The TES resistance can be monitored by voltage biasing and measuring the current through the TES. For example, a superconducting quantum interference device (SQUID) can be utilized in a known way for such monitoring. The increase in resistance with temperature leads to a reduction in measured current. With an ETF-TES system, the energy deposited in the TES is approximately the integral of the reduction in feedback Joule heating, or the bias voltage multiplied by the integral of the change in measured current. Alternatively, the TES resistance can be monitored by current biasing and measuring the voltage across the layers with a FET. There is a continuum of biasing conditions between voltage biasing and current biasing which can be used in the measurement. The superconducting transition can also be measured, for instance, via the change in the self- or mutual magnetic inductance of a coil or coils placed around the TES, or by a kinetic inductance measurement. The particle sensor can optionally include a heat pulse injector for calibration. The heat pulse can be injected by applying a current pulse to the absorber or TES. Further, description of an x-ray detector application for the inventive TES is provided, for example, in the above-cited Hilton et al. and Wollman et al. articles, as well as the Irwin et al. patent, all of which are incorporated by reference for such description and in their entirety.

The entire disclosure of all applications, patents and publications, cited above and below, and of corresponding Provisional Application Serial No. 60/157,741, filed Oct. 5, 1999 is hereby incorporated by reference.

In the foregoing and in the following examples, all temperatures are set forth uncorrected in degrees Kelvin; and, unless otherwise indicated, all parts and percentages are by weight.

EXAMPLES

Example 1

Figure 1:
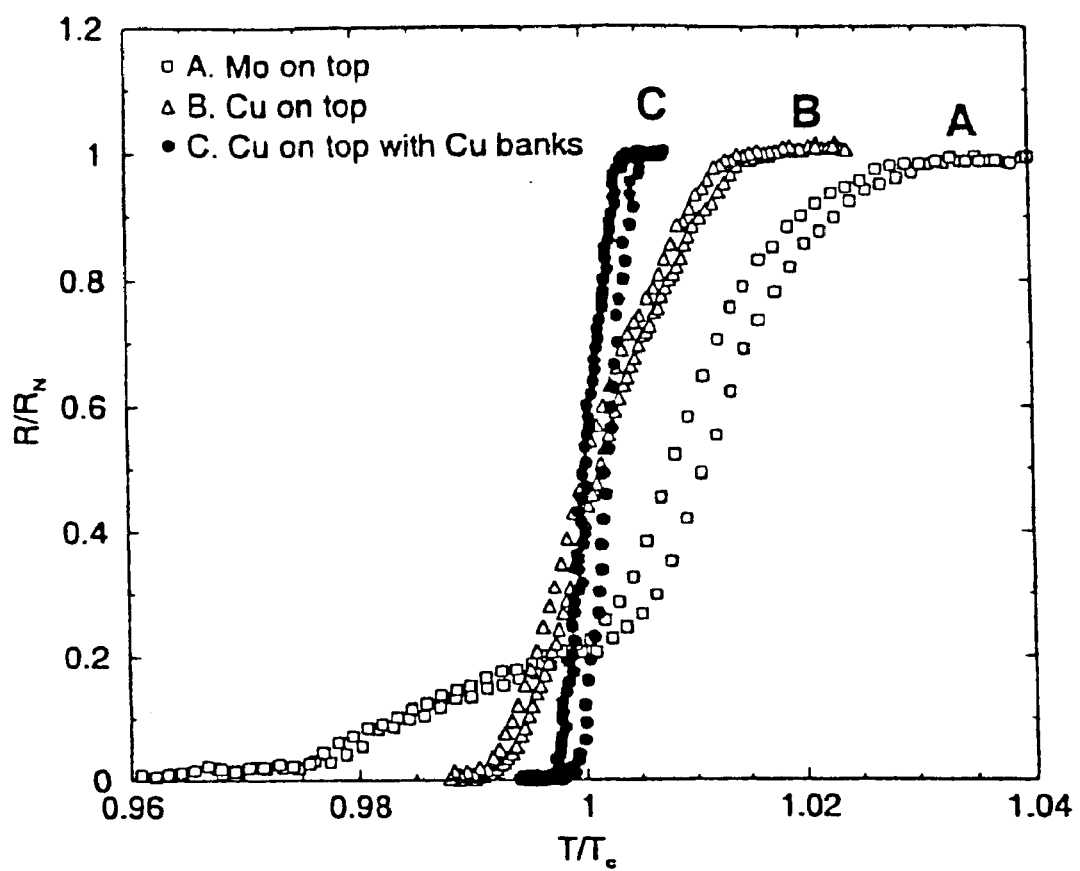
FIG. 1—Plots of the superconducting transitions for several varieties of Mo/Cu bilayers. Curve A: lower layer is Cu, upper layer is Mo. This sample has a broad transition with a pronounced knee, presumably due to stress effects. Curve B: lower layer is Mo, upper layer is Cu. This sample has a greatly improved transition, but still exhibits edge effects. Curve C: Mo on bottom Cu on top with Cu normal banks. This sample has a very narrow transition with no visible structure. All three samples have a transition temperature in the range of 230 mK to 270 mK. The data was taken by both heating and cooling the sample. The shift between traces is due to thermal settling in the measurement apparatus.
Figure 2:
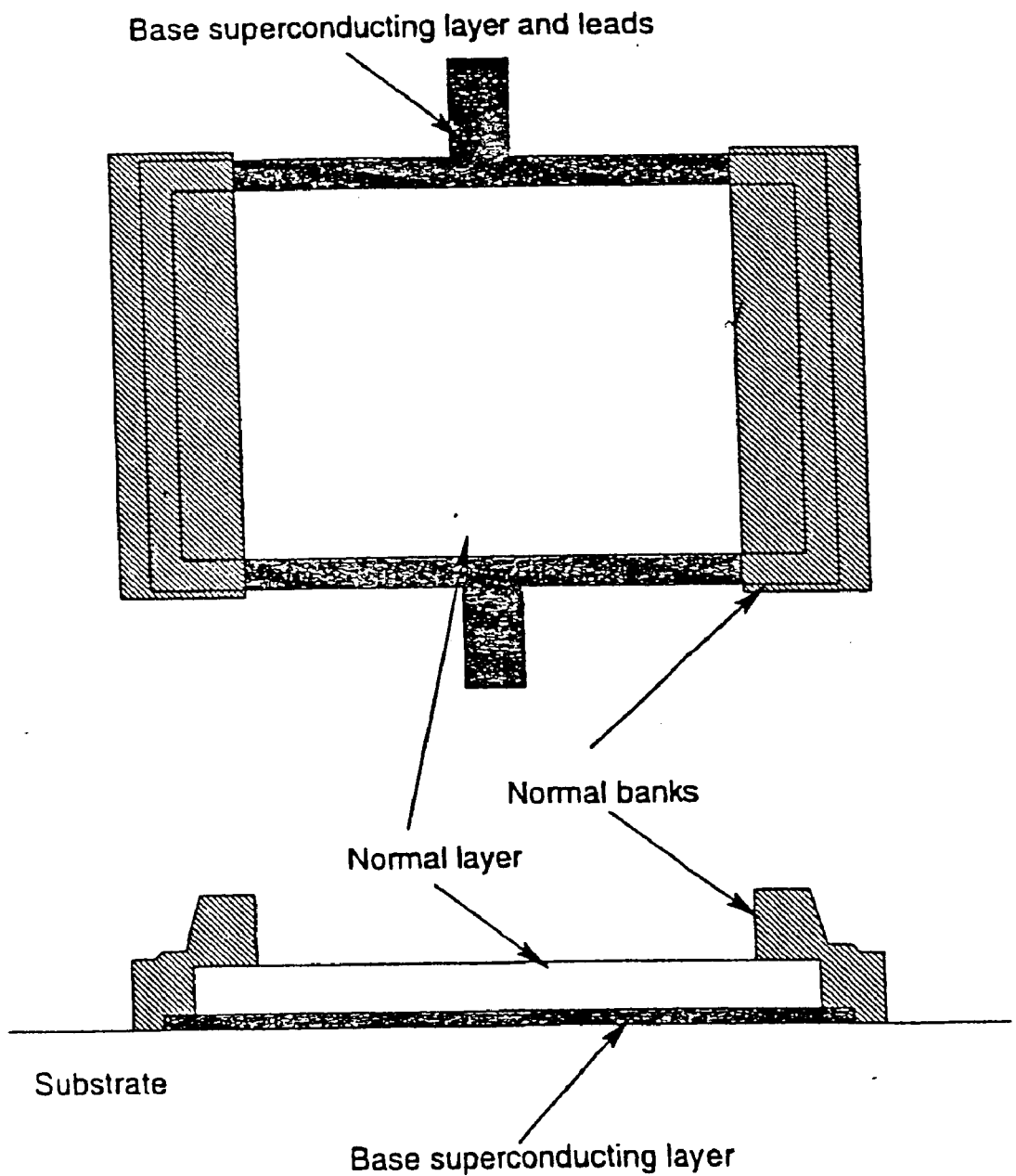
FIG. 2—Plan and cross-sectional views of bilayer TES with normal-metal boundary conditions supplied by additional normal-metal banks.

A TES having the structure schematically shown in FIG. 2 was fabricated by sputtering Mo as the superconducting TES layer and sputtering Cu as the normal TES layer. The two films were deposited in one pumping cycle to maintain a clean metallic interface and patterned by wet etching. The normal banks were then fabricated by e-beam evaporation of Cu through a lift-off stencil. Prior to depositing the banks, the exposed portions of the device were sputter cleaned. The thickness of the normal banks was chosen such that the region of the bank in contact with the superconducting base layer has a transition temperature significantly lower than the bulk of the TES. The superconducting transition of this structure is shown in FIG. 1C. The transition was very narrow with no visible structure, as desired.

Example 2

Figure 3:
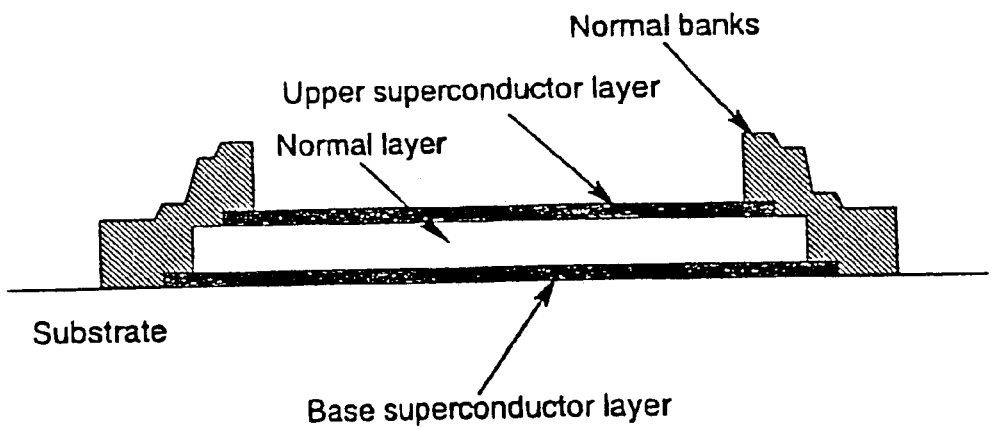
FIG. 3—Cross-sectional view of trilayer TES with normal-metal boundary conditions supplied by additional normal-metal banks.

A trilayer TES with normal metal banks structure, schematically shown in FIG. 3 can also be prepared. The use of a superconducting-normal-superconducting trilayer should increase the TES critical current, improving detector performance. In this example, the normal metal banks provide for normal boundary conditions, but do not fully passivate the TES edges due to the exposed superconducting/normal metal interface of the top layer. For a materials combination like Mo/Cu which exhibits low corrosion, this is likely to be acceptable. However, it may be desirable to put a thin layer of Cu on top and make a fully passivated quadlayer.

Example 3

Figure 4:
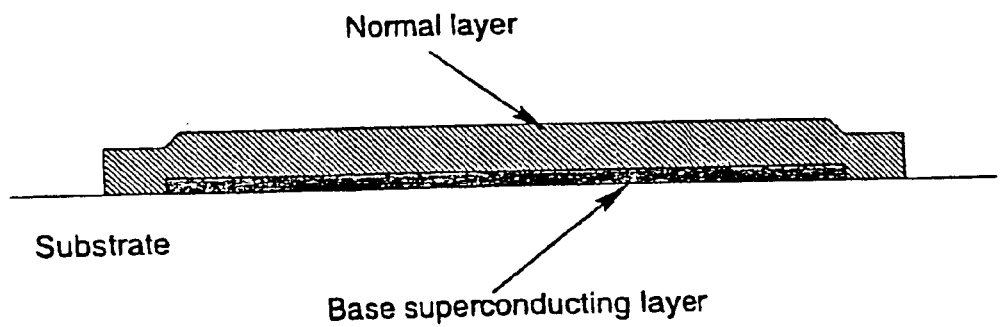
FIG. 4—Cross-sectional view of bilayer TES with integral normal-metal boundary conditions.
Figure 5:
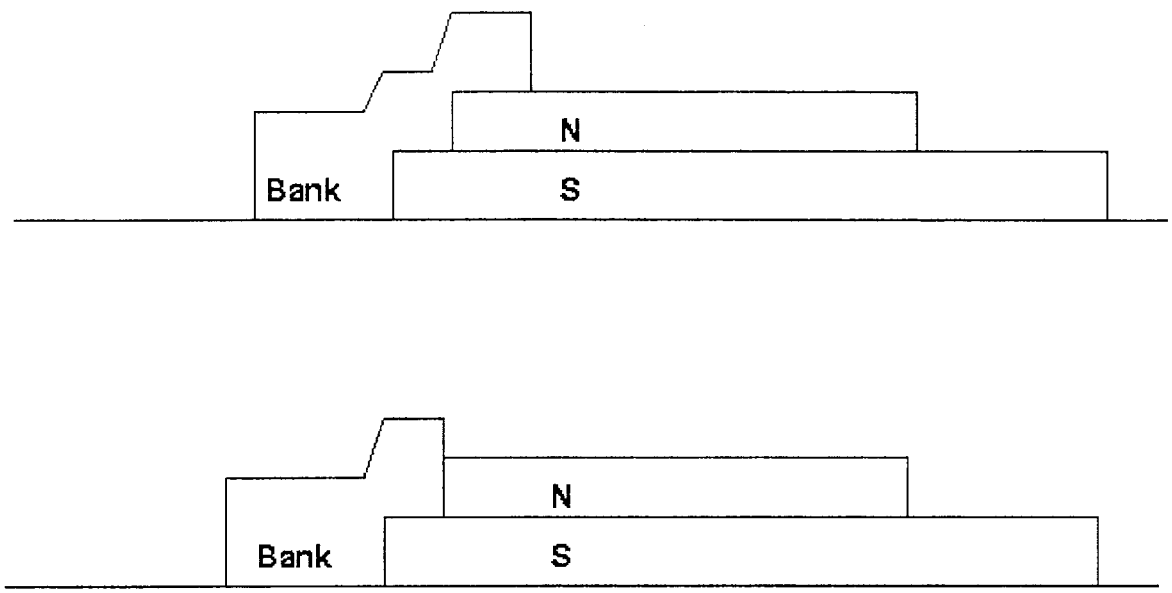
FIG. 5—Cross-sectional view of non-limiting structural alternatives for banks on bi-layer of normal metal (N) and superconductor (S).

FIG. 4 shows another variation using normal metal passivation. In order to make such a structure, it is necessary to deposit and pattern the two films of the bilayer separately, with the normal metal layer being deposited together with the banks. While we have made working bilayers by such a method, we find the bilayer properties are not optimally controlled by such a method. It is contemplated that suitable modifications can be made to optimize control for such bilayers.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Upon further study of the specification and appended claims, further objects and advantages of this invention will become apparent to those skilled in the art.

We claim:

1. A transition edge sensor comprising a structure of two or more metal layers on a substrate and electrical leads on outer sides of said structure, at least one of those layers being a normal metal layer and at least one of those layers being a superconducting metal layer, the at least one normal metal layer and superconducting metal layer overlaying each other, wherein at least two outer sides, other than the ones containing the electrical leads, of the at least one normal metal layer and the at least one superconducting metal layer and their corresponding outer interfaces are covered by a bank of normal metal.

2. The transition edge sensor of claim 1, wherein the structure of the layers is square, rectangular or trapezoidal, the leads are provided on opposing outer sides and the banks are provided on both outer sides not containing the leads.

3. The transition edge sensor of claim 1, wherein the banks result in normal-metal boundary conditions on the outer sides where they are provided.

4. The transition edge sensor of claim 1, which has a superconducting metal layer on the substrate and a normal metal layer on the superconducting layer.

5. The transition edge sensor of claim 4, wherein the banks are of the same normal metal as the normal metal layer.

6. The transition edge sensor of claim 5, wherein the banks and the normal metal layer are integrally formed in a single deposition step.

7. The transition edge sensor of claim 5, wherein the superconducting metal layer is elemental Mo; and, the normal metal layer is of copper, gold or silver.

8. The transition edge sensor of claim 4, wherein the normal metal layer has a smaller surface area than the superconducting metal layer and is contained within the periphery of the superconducting metal layer.

9. The transition edge sensor of claim 1, which has a superconducting metal layer on the substrate, a normal metal layer on the superconducting layer and a second superconducting layer on the normal metal layer.

10. The transition edge sensor of claim 1, wherein at least one superconducting metal layer is of elemental Mo, Ti, Al, Zr, W, Ir, Ta or Hf; at least one normal metal layer is of gold, silver, copper, palladium, platinum, a gold/copper alloy or a palladium/gold alloy; and the banks are of gold, silver, copper, palladium, platinum, a gold/copper alloy or a palladium/gold alloy.

11. The transition edge sensor of claim 1, wherein at least one superconducting metal layer is of elemental Mo or Ti; and, at least one normal metal layer is of copper, gold or silver.

12. The transition edge sensor of claim 1, wherein at least one superconducting metal layer has a thickness of 0.05 to 10 $\mu$m; and, at least one normal metal layer has a thickness of 0.05 to 10 $\mu$m.

13. The transition edge sensor of claim 1, wherein the superconducting transition temperature, $T_c$, of the sensor is from 50 to 500 mK.

14. The transition edge sensor of claim 1, wherein the width of the transition edge of the sensor is less than 0.1 mK.

15. A device comprising a precision thermometer where the thermometer is comprised of a transition edge sensor according to claim 1.

16. A particle or energy detector which comprises a transition edge sensor according to claim 1 and, in connection therewith, an absorber for absorbing the particle or energy, which absorber may be the transition edge sensor itself or some other component.

17. An x-ray microcalorimeter which comprises a transition edge sensor according to claim 1 and, in connection therewith, an absorber for absorbing x-rays, which absorber may be the transition edge sensor itself or some other component.

18. An x-ray microcalorimeter of claim 17, wherein the microcalorimeter is a spectrometer.

19. An x-ray microcalorimeter of claim 17, wherein the superconducting transition temperature, $T_c$, of the transition edge sensor is from 50 to 150 mK.

20. A transition edge sensor comprising a structure of two or more metal layers on a substrate and electrical leads on outer sides of said structure, at least one of those layers being a normal metal layer and at least one of those layers being a superconducting metal layer, the at least one normal metal layer and superconducting metal layer overlaying each other, wherein at least one outer side, other than the ones containing the electrical leads, of the at least one normal metal layer and the at least one superconducting metal layer and their corresponding outer interface are covered by a bank of normal metal.

21. The transition edge sensor of claim 20, wherein the at least one bank results in normal-metal boundary conditions on the outer side where it is provided.

22. The transition edge sensor of claim 20, which has a superconducting metal layer on the substrate and a normal metal layer on the superconducting layer.

23. The transition edge sensor of claim 22, wherein the at least one bank is of the same normal metal as the normal metal layer.

24. The transition edge sensor of claim 23, wherein the at least one bank and the normal metal layer are integrally formed in a single deposition step.

25. The transition edge sensor of claim 23, wherein the superconducting metal layer is elemental Mo; and, the normal metal layer is of copper, gold or silver.

26. The transition edge sensor of claim 22, wherein the normal metal layer has a smaller surface area than the superconducting metal layer and is contained within the periphery of the superconducting metal layer.

27. The transition edge sensor of claim 20, which has a superconducting metal layer on the substrate, a normal metal layer on the superconducting layer and a second superconducting layer on the normal metal layer.

28. The transition edge sensor of claim 20, wherein at least one superconducting metal layer is of elemental Mo, Ti, Al, Zr, W, Ir, Ta or Hf; at least one normal metal layer is of gold, silver, copper, palladium, platinum, a gold/copper alloy or a palladium/gold alloy; and the at least one bank is of gold, silver, copper, palladium, platinum, a gold/copper alloy or a palladium/gold alloy.

29. The transition edge sensor of claim 20, wherein at least one superconducting metal layer is of elemental Mo or Ti; and, at least one normal metal layer is of copper, gold or silver.

30. The transition edge sensor of claim 20, wherein at least one superconducting metal layer has a thickness of 0.05 to 10 $\mu$m; and, at least one normal metal layer has a thickness of 0.05 to 10 $\mu$m.

31. The transition edge sensor of claim 20, wherein the superconducting transition temperature, $T_c$, of the sensor is from 50 to 500 mK.

32. The transition edge sensor of claim 20, wherein the width of the transition edge of the sensor is less than 0.1 mK.

33. A device comprising a precision thermometer where the thermometer is comprised of a transition edge sensor according to claim 20.

34. A particle or energy detector which comprises a transition edge sensor according to claim 20 and, in connection therewith, an absorber for absorbing the particle or energy, which absorber may be the transition edge sensor itself or some other component.

35. An x-ray microcalorimeter which comprises a transition edge sensor according to claim 20 and, in connection therewith, an absorber for absorbing x-rays, which absorber may be the transition edge sensor itself or some other component.

36. An x-ray microcalorimeter of claim 35, wherein the microcalorimeter is a spectrometer.

37. An x-ray microcalorimeter of claim 35, wherein the superconducting transition temperature, $T_c$, of the transition edge sensor is from 50 to 150 mK.

* * * * *